US00PP11433P

United States Patent [19]

Fuess

[11] Patent Number: Plant 11,433

[45] Date of Patent: Jun. 27, 2000

[54] CHRYSANTHEMUM PLANT NAMED 'EMPIRE AMIGO'

[76] Inventor: Janet S. Fuess, 22 Country Club Dr., New York Mills, N.Y. 13417

[21] Appl. No.: 09/221,683

[22] Filed: Dec. 28, 1998

[51] Int. Cl.[7] ..... A01H 5/00

[52] U.S. Cl. ..... Plt./286

[58] Field of Search ..... Plt./286, 297, 298

*Primary Examiner*—Howard J. Locker

*Attorney, Agent, or Firm*—C. A. Whealy

[57] ABSTRACT

A distinct cultivar of Chrysanthemum plant named 'Empire Amigo', characterized by its semi-upright and mounding plant habit; daisy-type inflorescences that are about 5 to 5.5 cm in diameter; numerous attractive red purple ray florets; numerous inflorescences per plant; early flowering response; and excellent garden performance.

1 Drawing Sheet

BACKGROUND OF THE INVENTION

The present invention relates to a new and distinct cultivar of Chrysanthemum plant, botanically known as *Dendranthema grandiflora* and referred to by the cultivar name Empire Amigo.

The new cultivar is a product of a planned breeding program conducted by the Inventor in New Hartford, N.Y. The objective of the breeding program is to create new garden-type Chrysanthemum cultivars having inflorescences with desirable inflorescence forms and floret colors and good garden performance.

The new cultivar originated from a cross made by the Inventor in 1995, of the *Dendranthema grandiflora* cultivar Empire Crown Jewel, disclosed in U.S. Plant Pat. No. 9,738, as the female, or seed, parent with an proprietary seedling selection identified as C87-127 as the male, or pollen, parent, described as a purple daisy-type garden Chrysanthemum.

The cultivar Empire Amigo was discovered and selected by the Inventor as a flowering plant within the progeny of the stated cross in a controlled environment in New Hartford, N.Y., in September, 1996. The selection of this plant was based on its desirable inflorescence form and floret colors and excellent garden performance.

Asexual reproduction of the new cultivar by terminal cuttings taken in a controlled environment in New Hartford, N.Y., since October, 1996, has shown that the unique features of this new Chrysanthemum are stable and reproduced true to type in successive generations.

BRIEF SUMMARY OF THE INVENTION

The cultivar Empire Amigo has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Empire Amigo'. These characteristics in combination distinguish 'Empire Amigo' as a new and distinct cultivar:

1. Semi-upright and mounding plant habit.
2. Daisy-type inflorescences that are about 5 to 5.5 cm in diameter.
3. Numerous attractive red purple ray florets.
4. Numerous inflorescence per plant.
5. Early flowering response.
6. Excellent garden performance.

Plants of the new Chrysanthemum are similar in ray floret color to plants of the female parent, the cultivar Empire Crown Jewel. However in side-by-side comparisons in New Hartford, N.Y., under commercial practice, plants of the new Chrysanthemum were more upright and flowered about 10 days earlier under natural season flowering conditions than plants of the cultivar Empire Crown Jewel.

BRIEF DESCRIPTION OF THE PHOTOGRAPH

The accompanying photograph illustrates the overall appearance of the new cultivar. The photograph a side perspective view of a typical flowering plant of 'Empire Amigo'. This photograph shows the colors as true as it is reasonably possible to obtain in colored reproductions of this type. Floret and foliage colors in the photograph may differ from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in 20-cm containers in New Hartford, N.Y., under outdoor natural season conditions which approximate those generally used in commercial garden Chrysanthemum production. Measurements and comparisons were determined on Sep. 18, 1998 about mid-day under 4,000 foot-candles of light in New Hartford, N.Y.

Botanical classification: *Dendranthema grandiflora* cultivar Empire Amigo.

Commercial classification: Daisy-type garden chrysanthemum.

Parentage:

*Female or seed parent.*—*Dendranthema grandiflora* cultivar Empire Crown Jewel, disclosed in U.S. Plant Pat. No. 9,738.

*Male or pollen parent.*—Proprietary seedling selection identified as C87-127 and described as a purple daisy-type garden Chrysanthemum.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous daisy-type garden Chrysanthemum. Inverted triangle. Semi-upright and mounding. Freely branching. Flat capitulum form.

*Plant height.*—About 25 to 30 cm.

*Foliage description.*—Leaf arrangement: Alternate. Length: About 6.5 to 7 cm. Width: About 3.5 to 4 cm. Base: Attenuate. Margin: Palmate, five-lobed. Color: Mature foliage upper surface: 137B. Mature foliage lower surface: 137C.

Inflorescence description:

*Appearance.*—Daisy-type inflorescence form. Inflorescences borne on terminals above foliage, arising from leaf axils. Disk and ray florets arranged acropetally on a capitulum. One inflorescence per terminal with numerous inflorescences per plant.

*Flowering response.*—Under natural conditions, plants flower about Septemper 15th in New Hartford, N.Y. Plants exposed to artificially manipulated daylength will flower about 7 weeks after start of long nyctoperiod treatments.

*Inflorescence size.*—Diameter: About 5 to 5.5 cm.

*Ray florets.*—Length: About 2.6 cm. Width: About 8 mm. Number of ray florets per inflorescence: About 80 to 85. Color, opened inflorescence: Upper surface: Red purple, 74B. Lower surface: 74D.

*Disc florets.*—Shape: Tubular, apex dentate. Length: About 8 mm. Number of disc florets per inflorescence: About 120 to 125. Color: Immature: 6B. Mature: 15B.

*Reproductive organs.*—Androecium: Present on disc florets only; moderate pollen. Gynoecium: Present on both ray and disc florets.

Disease resistance: Resistance to known Chrysanthemum diseases has not been observed on plants grown under commercial production conditions.

Seed production: Seed production has not been observed.

It is claimed:

1. A new and distinct cultivar of Chrysanthemum plant named 'Empire Amigo', as illustrated and described.

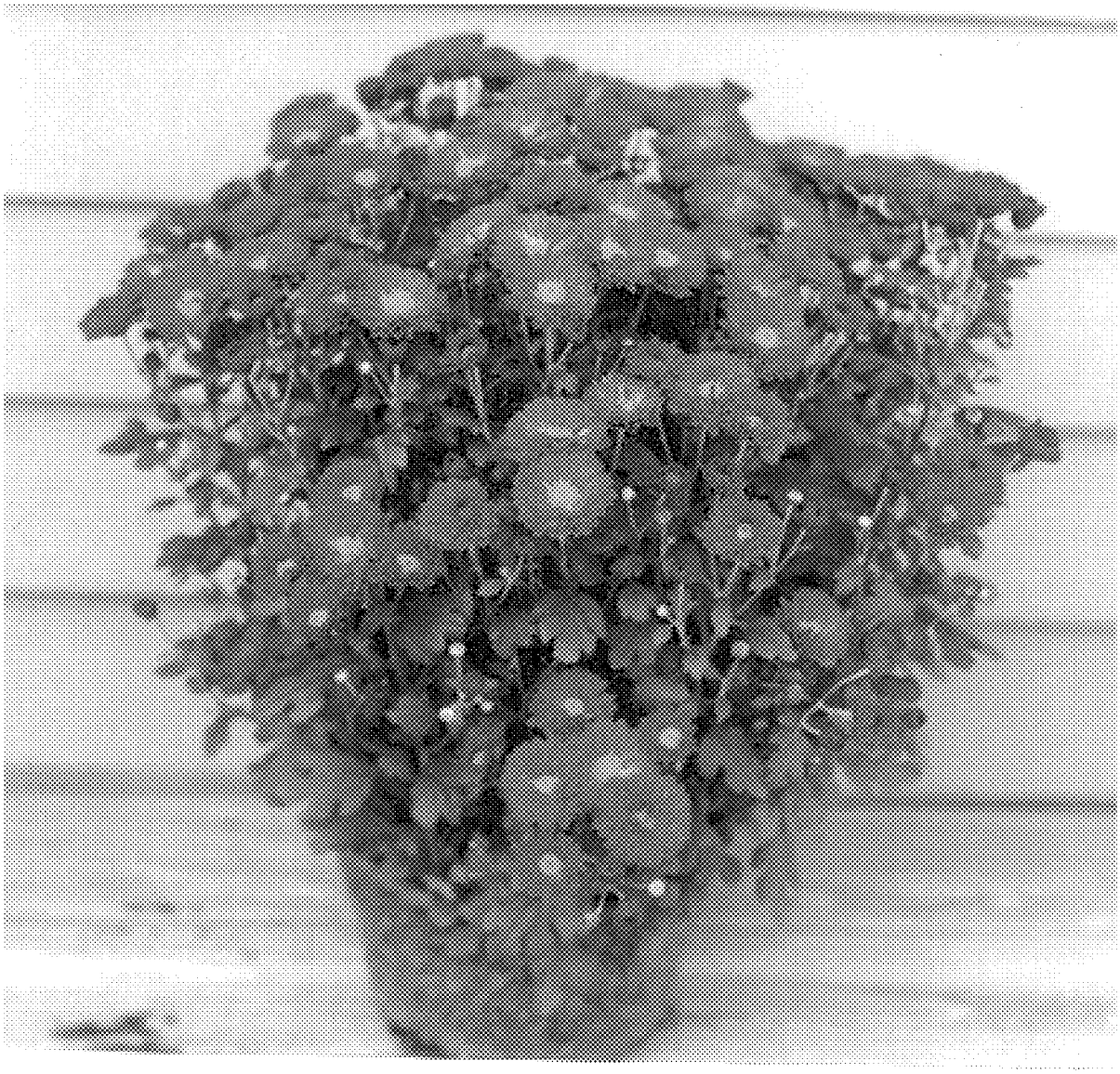

* * * * *